US005501975A

United States Patent [19]
Chaudhuri et al.

[11] Patent Number: 5,501,975
[45] Date of Patent: Mar. 26, 1996

[54] DNA MOLECULES ENCODING AN ER-LOCATED ENDOPROTEASE

[75] Inventors: Bhabatosh Chaudhuri, Münchenstein, Switzerland; Christine Stephan, Kingersheim, France; Peter Seeboth, Inzlingen, Germany; Howard Riezman, Biel-Benken, Switzerland

[73] Assignee: Ciba-Geigy Corporation, Tarrytown, N.Y.

[21] Appl. No.: 328,961

[22] Filed: Oct. 24, 1994

Related U.S. Application Data

[63] Continuation of Ser. No. 989,260, Dec. 11, 1992, abandoned.

[30] Foreign Application Priority Data

Dec. 16, 1991 [EP] European Pat. Off. ............... 91810984

[51] Int. Cl.⁶ .......................... C12N 15/62; C12N 15/63; C12N 15/57
[52] U.S. Cl. .................... 435/252.3; 536/23.4; 536/23.2; 435/223; 435/69.7; 435/69.8; 435/69.9; 435/320.1; 935/48; 935/10; 935/14
[58] Field of Search ....................... 435/223, 219, 435/69.7, 69.8, 69.9, 252.3, 320.1; 935/10, 14, 47, 48, 49; 536/23.2, 23.4

[56] References Cited

FOREIGN PATENT DOCUMENTS

| | | |
|---|---|---|
| 0205404 | 12/1986 | European Pat. Off. . |
| 0212914 | 3/1987 | European Pat. Off. . |
| 0277313 | 8/1988 | European Pat. Off. . |
| 0327377 | 8/1989 | European Pat. Off. . |

OTHER PUBLICATIONS

Pelham, H. R. B., "Evidence that luminal ER proteins are sorted from secreted proteins in a post–ER compartment", *The EMBO Journal*, 7(4): 913–918 (1988).

Barr et al., *J. Biol. Chem.*, 263:16471–16478 (1988).
Broach et al., *Gene*, 8:121–133 (1979).
Dean et al., *Biological Abstract* No. 91695, vol. 90, pp. 1006–1007 (1990).
Felgner et al., *Proc. Natl. Acad. Sci. USA*, 84:7413–7417 (1987).
Fuller et al., *Proc. Natl. Acad. Sci. USA*, 86:1434–1438 (1989).
Fuller et al., *Science*, 246:482–485 (1989).
Graham et al., *Virology*, 52:456–467 (1973).
Hinnen et al., "Heterologous Gene Expression in Yeast" in *Yeast Genetic Engineering*, pp. 193–213 (1989) Butterworths Publishers, Stoneham.
Klebe et al., *Gene*, 25:333–341 (1983).
Kurjan et al., *Cell*, 30:933–943 (1982).
Laemmli et al., *Nature*, 227:680–685 (1970).
Mizuno et al., *Biochem. Biophys. Res. Commun.*, 156:246–254 (1988).
Pfeffer et al., *Ann. Rev. Biochem.*, 56:829–852 (1987).
Rothstein, *Methods Enzymol.*, 194:281–302 (1991).
Sanger et al., *Proc. Natl. Acad. Sci. USA*, 74:5463–5467 (1977).
Steube et al., *Eur. J. Biochem.*, 198:651–657 (1991).
Von Heijne, *Nucleic Acids Research*, 14(11) 4683–4690 (1986).
Zoller et al., Methods in Enzymology, 154:329–350 (1987).
Mullenbach et al., *Fed. Proc.* 42:434 (abstract) (1983).
Chaudhuri et al., *FEBS Letters* 304:41–45 (1992).
Mitani et al., *Yeast*, 6:127–137 (1990).
Dean et al. *J. Cell. Biol.* vol. 111, Aug. 1990, pp. 369–377.

*Primary Examiner*—Charles L. Patterson, Jr.
*Assistant Examiner*—Keith D. Hendricks
*Attorney, Agent, or Firm*—James Scott Elmer

[57] ABSTRACT

The invention concerns novel DNA molecules encoding a modified, endoplasmic reticulum-located "dibasic processing endoprotease" and the use of said endoplasmic reticulum-located "dibasic processing endoprotease" for the correct processing of heterologous polypeptides in transformed hosts.

8 Claims, No Drawings

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 1866 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1866
        ( D ) OTHER INFORMATION: /product="soluble KEX2"

( x i ) SEQUENCE DESCRIPTION: SEQ ID NO:1:

```
ATG AAA GTG AGG AAA TAT ATT ACT TTA TGC TTT TGG TGG GCC TTT TCA    48
Met Lys Val Arg Lys Tyr Ile Thr Leu Cys Phe Trp Trp Ala Phe Ser
 1               5                  10                  15

ACA TCC GCT CTT GTA TCA TCA CAA CAA ATT CCA TTG AAG GAC CAT ACG    96
Thr Ser Ala Leu Val Ser Ser Gln Gln Ile Pro Leu Lys Asp His Thr
                20                  25                  30

TCA CGA CAG TAT TTT GCT GTA GAA AGC AAT GAA ACA TTA TCC CGC TTG   144
Ser Arg Gln Tyr Phe Ala Val Glu Ser Asn Glu Thr Leu Ser Arg Leu
            35                  40                  45

GAG GAA ATG CAT CCA AAT TGG AAA TAT GAA CAT GAT GTT CGA GGG CTA   192
Glu Glu Met His Pro Asn Trp Lys Tyr Glu His Asp Val Arg Gly Leu
        50                  55                  60

CCA AAC CAT TAT GTT TTT TCA AAA GAG TTG CTA AAA TTG GGC AAA AGA   240
Pro Asn His Tyr Val Phe Ser Lys Glu Leu Leu Lys Leu Gly Lys Arg
65                  70                  75                  80

TCA TCA TTA GAA GAG TTA CAG GGG GAT AAC AAC GAC CAC ATA TTA TCT   288
Ser Ser Leu Glu Glu Leu Gln Gly Asp Asn Asn Asp His Ile Leu Ser
                85                  90                  95

GTC CAT GAT TTA TTC CCG CGT AAC GAC CTA TTT AAG AGA CTA CCG GTG   336
Val His Asp Leu Phe Pro Arg Asn Asp Leu Phe Lys Arg Leu Pro Val
            100                 105                 110

CCT GCT CCA CCA ATG GAC TCA AGC TTG TTA CCG GTA AAA GAA GCT GAG   384
Pro Ala Pro Pro Met Asp Ser Ser Leu Leu Pro Val Lys Glu Ala Glu
        115                 120                 125

GAT AAA CTC AGC ATA AAT GAT CCG CTT TTT GAG AGG CAG TGG CAC TTG   432
Asp Lys Leu Ser Ile Asn Asp Pro Leu Phe Glu Arg Gln Trp His Leu
130                 135                 140

GTC AAT CCA AGT TTT CCT GGC AGT GAT ATA AAT GTT CTT GAT CTG TGG   480
Val Asn Pro Ser Phe Pro Gly Ser Asp Ile Asn Val Leu Asp Leu Trp
145                 150                 155                 160

TAC AAT AAT ATT ACA GGC GCA GGG GTC GTG GCT GCC ATT GTT GAT GAT   528
Tyr Asn Asn Ile Thr Gly Ala Gly Val Val Ala Ala Ile Val Asp Asp
                165                 170                 175

GGC CTT GAC TAC GAA AAT GAA GAC TTG AAG GAT AAT TTT TGC GCT GAA   576
Gly Leu Asp Tyr Glu Asn Glu Asp Leu Lys Asp Asn Phe Cys Ala Glu
            180                 185                 190
```

| | | | | | | | | | | | | | | | | |
|---|---|---|---|---|---|---|---|---|---|---|---|---|---|---|---|---|
| GGT | TCT | TGG | GAT | TTC | AAC | GAC | AAT | ACC | AAT | TTA | CCT | AAA | CCA | AGA | TTA | 624 |
| Gly | Ser | Trp | Asp | Phe | Asn | Asp | Asn | Thr | Asn | Leu | Pro | Lys | Pro | Arg | Leu | |
| | | 195 | | | | | 200 | | | | | 205 | | | | |
| TCT | GAT | GAC | TAC | CAT | GGT | ACG | AGA | TGT | GCA | GGT | GAA | ATA | GCT | GCC | AAA | 672 |
| Ser | Asp | Asp | Tyr | His | Gly | Thr | Arg | Cys | Ala | Gly | Glu | Ile | Ala | Ala | Lys | |
| | | 210 | | | | | 215 | | | | | 220 | | | | |
| AAA | GGT | AAC | AAT | TTT | TGC | GGT | GTC | GGG | GTA | GGT | TAC | AAC | GCT | AAA | ATC | 720 |
| Lys | Gly | Asn | Asn | Phe | Cys | Gly | Val | Gly | Val | Gly | Tyr | Asn | Ala | Lys | Ile | |
| 225 | | | | | 230 | | | | | 235 | | | | | 240 | |
| TCA | GGC | ATA | AGA | ATC | TTA | TCC | GGT | GAT | ATC | ACT | ACG | GAA | GAT | GAA | GCT | 768 |
| Ser | Gly | Ile | Arg | Ile | Leu | Ser | Gly | Asp | Ile | Thr | Thr | Glu | Asp | Glu | Ala | |
| | | | | 245 | | | | | 250 | | | | | 255 | | |
| GCG | TCC | TTG | ATT | TAT | GGT | CTA | GAC | GTA | AAC | GAT | ATA | TAT | TCA | TGC | TCA | 816 |
| Ala | Ser | Leu | Ile | Tyr | Gly | Leu | Asp | Val | Asn | Asp | Ile | Tyr | Ser | Cys | Ser | |
| | | | | 260 | | | | | 265 | | | | | 270 | | |
| TGG | GGT | CCC | GCT | GAT | GAC | GGA | AGA | CAT | TTA | CAA | GGC | CCT | AGT | GAC | CTG | 864 |
| Trp | Gly | Pro | Ala | Asp | Asp | Gly | Arg | His | Leu | Gln | Gly | Pro | Ser | Asp | Leu | |
| | | 275 | | | | | 280 | | | | | 285 | | | | |
| GTG | AAA | AAG | GCT | TTA | GTA | AAA | GGT | GTT | ACT | GAG | GGA | AGA | GAT | TCC | AAA | 912 |
| Val | Lys | Lys | Ala | Leu | Val | Lys | Gly | Val | Thr | Glu | Gly | Arg | Asp | Ser | Lys | |
| | | 290 | | | | | 295 | | | | | 300 | | | | |
| GGA | GCG | ATT | TAC | GTT | TTT | GCC | AGT | GGA | AAT | GGT | GGA | ACT | CGT | GGT | GAT | 960 |
| Gly | Ala | Ile | Tyr | Val | Phe | Ala | Ser | Gly | Asn | Gly | Gly | Thr | Arg | Gly | Asp | |
| 305 | | | | | 310 | | | | | 315 | | | | | 320 | |
| AAT | TGC | AAT | TAC | GAC | GGC | TAT | ACT | AAT | TCC | ATA | TAT | TCT | ATT | ACT | ATT | 1008 |
| Asn | Cys | Asn | Tyr | Asp | Gly | Tyr | Thr | Asn | Ser | Ile | Tyr | Ser | Ile | Thr | Ile | |
| | | | | 325 | | | | | 330 | | | | | 335 | | |
| GGG | GCT | ATT | GAT | CAC | AAA | GAT | CTA | CAT | CCT | CCT | TAT | TCC | GAA | GGT | TGT | 1056 |
| Gly | Ala | Ile | Asp | His | Lys | Asp | Leu | His | Pro | Pro | Tyr | Ser | Glu | Gly | Cys | |
| | | | | 340 | | | | | 345 | | | | | 350 | | |
| TCC | GCC | GTC | ATG | GCA | GTC | ACG | TAT | TCT | TCA | GGT | TCA | GGC | GAA | TAT | ATT | 1104 |
| Ser | Ala | Val | Met | Ala | Val | Thr | Tyr | Ser | Ser | Gly | Ser | Gly | Glu | Tyr | Ile | |
| | | | 355 | | | | | 360 | | | | | 365 | | | |
| CAT | TCG | AGT | GAT | ATC | AAC | GGC | AGA | TGC | AGT | AAT | AGC | CAC | GGT | GGA | ACG | 1152 |
| His | Ser | Ser | Asp | Ile | Asn | Gly | Arg | Cys | Ser | Asn | Ser | His | Gly | Gly | Thr | |
| | 370 | | | | | 375 | | | | | 380 | | | | | |
| TCT | GCG | GCT | GCT | CCA | TTA | GCT | GCC | GGT | GTT | TAC | ACT | TTG | TTA | CTA | GAA | 1200 |
| Ser | Ala | Ala | Ala | Pro | Leu | Ala | Ala | Gly | Val | Tyr | Thr | Leu | Leu | Leu | Glu | |
| 385 | | | | 390 | | | | | 395 | | | | | 400 | | |
| GCC | AAC | CCA | AAC | CTA | ACT | TGG | AGA | GAC | GTA | CAG | TAT | TTA | TCA | ATC | TTG | 1248 |
| Ala | Asn | Pro | Asn | Leu | Thr | Trp | Arg | Asp | Val | Gln | Tyr | Leu | Ser | Ile | Leu | |
| | | | | 405 | | | | | 410 | | | | | 415 | | |
| TCT | GCG | GTA | GGG | TTA | GAA | AAG | AAC | GCT | GAC | GGA | GAT | TGG | AGA | GAT | AGC | 1296 |
| Ser | Ala | Val | Gly | Leu | Glu | Lys | Asn | Ala | Asp | Gly | Asp | Trp | Arg | Asp | Ser | |
| | | | 420 | | | | | 425 | | | | | 430 | | | |
| GCC | ATG | GGG | AAG | AAA | TAC | TCT | CAT | CGC | TAT | GGC | TTT | GGT | AAA | ATC | GAT | 1344 |
| Ala | Met | Gly | Lys | Lys | Tyr | Ser | His | Arg | Tyr | Gly | Phe | Gly | Lys | Ile | Asp | |
| | | 435 | | | | | 440 | | | | | 445 | | | | |
| GCC | CAT | AAG | TTA | ATT | GAA | ATG | TCC | AAG | ACC | TGG | GAG | AAT | GTT | AAC | GCA | 1392 |
| Ala | His | Lys | Leu | Ile | Glu | Met | Ser | Lys | Thr | Trp | Glu | Asn | Val | Asn | Ala | |
| | 450 | | | | | 455 | | | | | 460 | | | | | |
| CAA | ACC | TGG | TTT | TAC | CTG | CCA | ACA | TTG | TAT | GTT | TCC | CAG | TCC | ACA | AAC | 1440 |
| Gln | Thr | Trp | Phe | Tyr | Leu | Pro | Thr | Leu | Tyr | Val | Ser | Gln | Ser | Thr | Asn | |
| 465 | | | | | 470 | | | | | 475 | | | | | 480 | |
| TCC | ACG | GAA | GAG | ACA | TTA | GAA | TCC | GTC | ATA | ACC | ATA | TCA | GAA | AAA | AGT | 1488 |
| Ser | Thr | Glu | Glu | Thr | Leu | Glu | Ser | Val | Ile | Thr | Ile | Ser | Glu | Lys | Ser | |
| | | | | 485 | | | | | 490 | | | | | 495 | | |
| CTT | CAA | GAT | GCT | AAC | TTC | AAG | AGA | ATT | GAG | CAC | GTC | ACG | GTA | ACT | GTA | 1536 |
| Leu | Gln | Asp | Ala | Asn | Phe | Lys | Arg | Ile | Glu | His | Val | Thr | Val | Thr | Val | |
| | | | 500 | | | | | 505 | | | | | 510 | | | |

```
GAT  ATT  GAT  ACA  GAA  ATT  AGG  GGA  ACT  ACG  ACT  GTC  GAT  TTA  ATA  TCA    1584
Asp  Ile  Asp  Thr  Glu  Ile  Arg  Gly  Thr  Thr  Thr  Val  Asp  Leu  Ile  Ser
          515                      520                      525

CCA  GCG  GGG  ATA  ATT  TCA  AAC  CTT  GGC  GTT  GTA  AGA  CCA  AGA  GAT  GTT    1632
Pro  Ala  Gly  Ile  Ile  Ser  Asn  Leu  Gly  Val  Val  Arg  Pro  Arg  Asp  Val
     530                      535                      540

TCA  TCA  GAG  GGA  TTC  AAA  GAC  TGG  ACA  TTC  ATG  TCT  GTA  GCA  CAT  TGG    1680
Ser  Ser  Glu  Gly  Phe  Lys  Asp  Trp  Thr  Phe  Met  Ser  Val  Ala  His  Trp
545                 550                      555                           560

GGT  GAG  AAC  GGC  GTA  GGT  GAT  TGG  AAA  ATC  AAG  GTT  AAG  ACA  ACA  GAA    1728
Gly  Glu  Asn  Gly  Val  Gly  Asp  Trp  Lys  Ile  Lys  Val  Lys  Thr  Thr  Glu
               565                      570                      575

AAT  GGA  CAC  AGG  ATT  GAC  TTC  CAC  AGT  TGG  AGG  CTG  AAG  CTC  TTT  GGG    1776
Asn  Gly  His  Arg  Ile  Asp  Phe  His  Ser  Trp  Arg  Leu  Lys  Leu  Phe  Gly
          580                      585                           590

GAA  TCC  ATT  GAT  TCA  TCT  AAA  ACA  GAA  ACT  TTC  GTC  TTT  GGA  AAC  GAT    1824
Glu  Ser  Ile  Asp  Ser  Ser  Lys  Thr  Glu  Thr  Phe  Val  Phe  Gly  Asn  Asp
               595                      600                      605

AAA  GAG  GAG  GTT  GAA  CCA  GGG  GTA  CCG  AGC  TCG  AAT  TCG  TAA             1866
Lys  Glu  Glu  Val  Glu  Pro  Gly  Val  Pro  Ser  Ser  Asn  Ser
     610                      615                      620
```

( 2 ) INFORMATION FOR SEQ ID NO:2:

( i ) SEQUENCE CHARACTERISTICS:
        ( A ) LENGTH: 621 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Lys  Val  Arg  Lys  Tyr  Ile  Thr  Leu  Cys  Phe  Trp  Trp  Ala  Phe  Ser
1                        5                        10                       15

Thr  Ser  Ala  Leu  Val  Ser  Ser  Gln  Gln  Ile  Pro  Leu  Lys  Asp  His  Thr
               20                       25                       30

Ser  Arg  Gln  Tyr  Phe  Ala  Val  Glu  Ser  Asn  Glu  Thr  Leu  Ser  Arg  Leu
          35                       40                       45

Glu  Glu  Met  His  Pro  Asn  Trp  Lys  Tyr  Glu  His  Asp  Val  Arg  Gly  Leu
     50                       55                       60

Pro  Asn  His  Tyr  Val  Phe  Ser  Lys  Glu  Leu  Leu  Lys  Leu  Gly  Lys  Arg
65                       70                       75                       80

Ser  Ser  Leu  Glu  Glu  Leu  Gln  Gly  Asp  Asn  Asn  Asp  His  Ile  Leu  Ser
               85                       90                       95

Val  His  Asp  Leu  Phe  Pro  Arg  Asn  Asp  Leu  Phe  Lys  Arg  Leu  Pro  Val
               100                      105                      110

Pro  Ala  Pro  Pro  Met  Asp  Ser  Ser  Leu  Leu  Pro  Val  Lys  Glu  Ala  Glu
          115                      120                      125

Asp  Lys  Leu  Ser  Ile  Asn  Asp  Pro  Leu  Phe  Glu  Arg  Gln  Trp  His  Leu
     130                      135                      140

Val  Asn  Pro  Ser  Phe  Pro  Gly  Ser  Asp  Ile  Asn  Val  Leu  Asp  Leu  Trp
145                      150                      155                      160

Tyr  Asn  Asn  Ile  Thr  Gly  Ala  Gly  Val  Val  Ala  Ala  Ile  Val  Asp  Asp
               165                      170                      175

Gly  Leu  Asp  Tyr  Glu  Asn  Glu  Asp  Leu  Lys  Asp  Asn  Phe  Cys  Ala  Glu
          180                      185                      190

Gly  Ser  Trp  Asp  Phe  Asn  Asp  Asn  Thr  Asn  Leu  Pro  Lys  Pro  Arg  Leu
          195                      200                      205

Ser  Asp  Asp  Tyr  His  Gly  Thr  Arg  Cys  Ala  Gly  Glu  Ile  Ala  Ala  Lys
```

|         |         |         |         | 210     |         |         |         | 215     |         |         |         | 220     |         |         |         |
|---------|---------|---------|---------|---------|---------|---------|---------|---------|---------|---------|---------|---------|---------|---------|---------|

Lys Gly Asn Asn Phe Cys Gly Val Gly Val Gly Tyr Asn Ala Lys Ile
225                     230                     235                     240

Ser Gly Ile Arg Ile Leu Ser Gly Asp Ile Thr Thr Glu Asp Glu Ala
            245                     250                     255

Ala Ser Leu Ile Tyr Gly Leu Asp Val Asn Asp Ile Tyr Ser Cys Ser
            260                     265                     270

Trp Gly Pro Ala Asp Asp Gly Arg His Leu Gln Gly Pro Ser Asp Leu
        275                     280                     285

Val Lys Lys Ala Leu Val Lys Gly Val Thr Glu Gly Arg Asp Ser Lys
    290                     295                     300

Gly Ala Ile Tyr Val Phe Ala Ser Gly Asn Gly Gly Thr Arg Gly Asp
305                     310                     315                     320

Asn Cys Asn Tyr Asp Gly Tyr Thr Asn Ser Ile Tyr Ser Ile Thr Ile
                325                     330                     335

Gly Ala Ile Asp His Lys Asp Leu His Pro Pro Tyr Ser Glu Gly Cys
            340                     345                     350

Ser Ala Val Met Ala Val Thr Tyr Ser Ser Gly Ser Gly Glu Tyr Ile
        355                     360                     365

His Ser Ser Asp Ile Asn Gly Arg Cys Ser Asn Ser His Gly Gly Thr
    370                     375                     380

Ser Ala Ala Ala Pro Leu Ala Ala Gly Val Tyr Thr Leu Leu Leu Glu
385                     390                     395                     400

Ala Asn Pro Asn Leu Thr Trp Arg Asp Val Gln Tyr Leu Ser Ile Leu
                405                     410                     415

Ser Ala Val Gly Leu Glu Lys Asn Ala Asp Gly Asp Trp Arg Asp Ser
            420                     425                     430

Ala Met Gly Lys Lys Tyr Ser His Arg Tyr Gly Phe Gly Lys Ile Asp
        435                     440                     445

Ala His Lys Leu Ile Glu Met Ser Lys Thr Trp Glu Asn Val Asn Ala
    450                     455                     460

Gln Thr Trp Phe Tyr Leu Pro Thr Leu Tyr Val Ser Gln Ser Thr Asn
465                     470                     475                     480

Ser Thr Glu Glu Thr Leu Glu Ser Val Ile Thr Ile Ser Glu Lys Ser
                485                     490                     495

Leu Gln Asp Ala Asn Phe Lys Arg Ile Glu His Val Thr Val Thr Val
            500                     505                     510

Asp Ile Asp Thr Glu Ile Arg Gly Thr Thr Thr Val Asp Leu Ile Ser
    515                     520                     525

Pro Ala Gly Ile Ile Ser Asn Leu Gly Val Val Arg Pro Arg Asp Val
530                     535                     540

Ser Ser Glu Gly Phe Lys Asp Trp Thr Phe Met Ser Val Ala His Trp
545                     550                     555                     560

Gly Glu Asn Gly Val Gly Asp Trp Lys Ile Lys Val Lys Thr Thr Glu
                565                     570                     575

Asn Gly His Arg Ile Asp Phe His Ser Trp Arg Leu Lys Leu Phe Gly
            580                     585                     590

Glu Ser Ile Asp Ser Ser Lys Thr Glu Thr Phe Val Phe Gly Asn Asp
        595                     600                     605

Lys Glu Glu Val Glu Pro Gly Val Pro Ser Ser Asn Ser
    610                     615                     620

( 2 ) INFORMATION FOR SEQ ID NO:3:

( i ) SEQUENCE CHARACTERISTICS:
   ( A ) LENGTH: 12 base pairs
   ( B ) TYPE: nucleic acid
   ( C ) STRANDEDNESS: double
   ( D ) TOPOLOGY: linear ( i i ) MOLECULE TYPE: DNA (genomic)

( i x ) FEATURE:
   ( A ) NAME/KEY: CDS
   ( B ) LOCATION: 1..12
   ( D ) OTHER INFORMATION: /function="coding region for ER
    retention signal HDEL"

( x i ) SEQUENCE DESCRIPTION: SEQ ID NO:3:

```
CAC  GAC  GAA  TTA                                                          12
His  Asp  Glu  Leu
 1
```

( 2 ) INFORMATION FOR SEQ ID NO:4:

( i ) SEQUENCE CHARACTERISTICS:
   ( A ) LENGTH: 4 amino acids
   ( B ) TYPE: amino acid
   ( D ) TOPOLOGY: linear ( i i ) MOLECULE TYPE: protein ( x i ) SEQUENCE DESCRIPTION: SEQ ID NO:4:

```
His  Asp  Glu  Leu
 1
```

( 2 ) INFORMATION FOR SEQ ID NO:5:

( i ) SEQUENCE CHARACTERISTICS:
   ( A ) LENGTH: 4 amino acids
   ( B ) TYPE: amino acid
   ( D ) TOPOLOGY: linear ( i i ) MOLECULE TYPE: peptide ( v i ) ORIGINAL SOURCE:
   ( A ) ORGANISM: Kluyveromyces lactis ( i x ) FEATURE:
   ( A ) NAME/KEY: Domain
   ( B ) LOCATION: 1..4
   ( D ) OTHER INFORMATION: /note="ER retention signal DDEL"

( x i ) SEQUENCE DESCRIPTION: SEQ ID NO:5:

```
 Asp  Asp  Glu  Leu
  1
```

( 2 ) INFORMATION FOR SEQ ID NO:6:

( i ) SEQUENCE CHARACTERISTICS:
   ( A ) LENGTH: 4 amino acids
   ( B ) TYPE: amino acid
   ( D ) TOPOLOGY: linear ( i i ) MOLECULE TYPE: peptide ( i x ) FEATURE:
   ( A ) NAME/KEY: Domain
   ( B ) LOCATION: 1..4
   ( D ) OTHER INFORMATION: /note="ER retention signal KDEL"

( x i ) SEQUENCE DESCRIPTION: SEQ ID NO:6:

```
 Lys  Asp  Glu  Leu
  1
```

( 2 ) INFORMATION FOR SEQ ID NO:7:

( i ) SEQUENCE CHARACTERISTICS:
  ( A ) LENGTH: 1158 base pairs
  ( B ) TYPE: nucleic acid
  ( C ) STRANDEDNESS: double
  ( D ) TOPOLOGY: linear ( i i ) MOLECULE TYPE: DNA (genomic)

( i x ) FEATURE:
  ( A ) NAME/KEY: CDS
  ( B ) LOCATION: 405..869

( x i ) SEQUENCE DESCRIPTION: SEQ ID NO:7:

| | | | | | | |
|---|---|---|---|---|---|---|
| GGATCCCCAG | CTTAGTTCAT | AGGTCCATTC | TCTTAGCGCA | ACTACAGAGA | ACAGGGGCAC | 60 |
| AAACAGGCAA | AAAACGGGCA | CAACCTCAAT | GGAGTGATGC | AACCTGCCTG | GAGTAAATGA | 120 |
| TGACACAAGG | CAATTGACCC | ACGCATGTAT | CTATCTCATT | TTCTTACACC | TTCTATTACC | 180 |
| TTCTGCTCTC | TCTGATTTGG | AAAAAGCTGA | AAAAAAGGT | TGAAACCAGT | TCCCTGAAAT | 240 |
| TATTCCCCTA | CTTGACTAAT | AAGTATATAA | AGACGGTAGG | TATTGATTGT | AATTCTGTAA | 300 |
| ATCTATTTCT | TAAACTTCTT | AAATTCTACT | TTTATAGTTA | GTCTTTTTT | TAGTTTTAAA | 360 |
| ACACCAAGAA | CTTAGTTTCG | AATAAACACA | CATAAACAAA | CACC ATG AGA TTT CCT | | 416 |
| | | | | Met Arg Phe Pro | | |
| | | | | 1 | | |

```
TCA  ATT  TTT  ACT  GCA  GTT  TTA  TTC  GCA  GCA  TCC  TCC  GCA  TTA  GCT  GCT    464
Ser  Ile  Phe  Thr  Ala  Val  Leu  Phe  Ala  Ala  Ser  Ser  Ala  Leu  Ala  Ala
 5               10                    15                        20

CCA  GTC  AAC  ACT  ACA  ACA  GAA  GAT  GAA  ACG  GCA  CAA  ATT  CCG  GCT  GAA    512
Pro  Val  Asn  Thr  Thr  Thr  Glu  Asp  Glu  Thr  Ala  Gln  Ile  Pro  Ala  Glu
                     25                    30                        35

GCT  GTC  ATC  GGT  TAC  TTA  GAT  TTA  GAA  GGG  GAT  TTC  GAT  GTT  GCT  GTT    560
Ala  Val  Ile  Gly  Tyr  Leu  Asp  Leu  Glu  Gly  Asp  Phe  Asp  Val  Ala  Val
                40                    45                        50

TTG  CCA  TTT  TCC  AAC  AGC  ACA  AAT  AAC  GGG  TTA  TTG  TTT  ATA  AAT  ACT    608
Leu  Pro  Phe  Ser  Asn  Ser  Thr  Asn  Asn  Gly  Leu  Leu  Phe  Ile  Asn  Thr
           55                    60                        65

ACT  ATT  GCC  AGC  ATT  GCT  GCT  AAA  GAA  GAA  GGG  GTA  CAG  CTG  GAT  AAA    656
Thr  Ile  Ala  Ser  Ile  Ala  Ala  Lys  Glu  Glu  Gly  Val  Gln  Leu  Asp  Lys
     70                    75                        80

AGA  GGT  CCA  GAA  ACC  TTG  TGT  GGT  GCT  GAA  TTG  GTC  GAT  GCT  TTG  CAA    704
Arg  Gly  Pro  Glu  Thr  Leu  Cys  Gly  Ala  Glu  Leu  Val  Asp  Ala  Leu  Gln
 85                    90                    95                       100

TTC  GTT  TGT  GGT  GAC  AGA  GGT  TTC  TAC  TTC  AAC  AAG  CCA  ACC  GGT  TAC    752
Phe  Val  Cys  Gly  Asp  Arg  Gly  Phe  Tyr  Phe  Asn  Lys  Pro  Thr  Gly  Tyr
                    105                   110                       115

GGT  TCT  TCT  TCT  AGA  AGA  GCT  CCA  CAA  ACC  GGT  ATC  GTT  GAC  GAA  TGT    800
Gly  Ser  Ser  Ser  Arg  Arg  Ala  Pro  Gln  Thr  Gly  Ile  Val  Asp  Glu  Cys
                120                   125                       130

TGT  TTC  AGA  TCT  TGT  GAC  TTG  AGA  AGA  TTG  GAA  ATG  TAC  TGT  GCT  CCA    848
Cys  Phe  Arg  Ser  Cys  Asp  Leu  Arg  Arg  Leu  Glu  Met  Tyr  Cys  Ala  Pro
          135                   140                       145

TTG  AAG  CCA  GCT  AAG  TCT  GCT  TGATAAGTCG  ACTTTGTTCC  CACTGTACTT             899
Leu  Lys  Pro  Ala  Lys  Ser  Ala
          150                   155
```

| | | | | | | |
|---|---|---|---|---|---|---|
| TTAGCTCGTA | CAAAATACAA | TATACTTTTC | ATTTCTCCGT | AAACAACATG | TTTTCCCATG | 959 |
| TAATATCCTT | TTCTATTTTT | CGTTCCGTTA | CCAACTTTAC | ACATACTTTA | TATAGCTATT | 1019 |
| CACTTCTATA | CACTAAAAAA | CTAAGACAAT | TTTAATTTTG | CTGCCTGCCA | TATTTCAATT | 1079 |
| TGTTATAAAT | TCCTATAATT | TATCCTATTA | GTAGCTAAAA | AAAGATGAAT | GTGAATCGAA | 1139 |
| TCCTAAGAGA | ATTGGATCC | | | | | 1158 |

( 2 ) INFORMATION FOR SEQ ID NO:8:

( i ) SEQUENCE CHARACTERISTICS:
        ( A ) LENGTH: 155 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Arg Phe Pro Ser Ile Phe Thr Ala Val Leu Phe Ala Ala Ser Ser
 1               5                  10                  15
Ala Leu Ala Ala Pro Val Asn Thr Thr Thr Glu Asp Glu Thr Ala Gln
                20                  25                  30
Ile Pro Ala Glu Ala Val Ile Gly Tyr Leu Asp Leu Glu Gly Asp Phe
            35                  40                  45
Asp Val Ala Val Leu Pro Phe Ser Asn Ser Thr Asn Asn Gly Leu Leu
        50                  55                  60
Phe Ile Asn Thr Thr Ile Ala Ser Ile Ala Ala Lys Glu Glu Gly Val
65                  70                  75                  80
Gln Leu Asp Lys Arg Gly Pro Glu Thr Leu Cys Gly Ala Glu Leu Val
                85                  90                  95
Asp Ala Leu Gln Phe Val Cys Gly Asp Arg Gly Phe Tyr Phe Asn Lys
                100                 105                 110
Pro Thr Gly Tyr Gly Ser Ser Ser Arg Arg Ala Pro Gln Thr Gly Ile
            115                 120                 125
Val Asp Glu Cys Cys Phe Arg Ser Cys Asp Leu Arg Arg Leu Glu Met
        130                 135                 140
Tyr Cys Ala Pro Leu Lys Pro Ala Lys Ser Ala
145                 150                 155
```

( 2 ) INFORMATION FOR SEQ ID NO:9:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GTAGTGTTGA CTAGATCTGC TAATGCGGAG G           31

( 2 ) INFORMATION FOR SEQ ID NO:10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GCGGAGGATG CGTTGAATAA AACTGC           26

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: single -continued ( D ) TOPOLOGY: linear ( i i ) MOLECULE TYPE: DNA (genomic)

( x i ) SEQUENCE DESCRIPTION: SEQ ID NO:11:

CAGCTTCAGC AGTAATGTTT GCCGTTTC  28

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

ATCTAAGTAG TTGATGACAG C  21

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GCTGTACCCC GGTTTCGTTA GCAGCAATGC  30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GTACCGTTCG AACACGACGA ATTATAATAG  30

( 2 ) INFORMATION FOR SEQ ID NO:15:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AATTCTATTA TAATTCGTCG TGTTCGAACG  30

DNA MOLECULES ENCODING AN ER-LOCATED ENDOPROTEASE

This application is a continuation of application Ser. No. 07/989,260, filed Dec. 11, 1992, now abandoned.

The invention concerns novel DNA molecules encoding a modified, endoplasmic reticulum-located "dibasic processing endoprotease" and the use of said endoplasmic reticulum-located "dibasic processing endoprotease" for the correct processing of heterologous polypeptides in transformed hosts.

BACKGROUND OF THE INVENTION

The production of pharmaceutically applicable or enzymatically active proteins is a key area in the rapidly developing biotechnology industry. Since the beginning of the era of recombinant DNA technology a great number of valuable heterologous proteins have been produced in and secreted from eukaryotic host cells which had been transformed with suitable expression vectors containing DNA sequences coding for said proteins. One of the major problems with the production of secreted proteins in eukaryotic expression systems is to avoid malfolded biologically inactive product.

It is now generally accepted that proteins destined for secretion from eukaryotic cells are translocated to the endoplasmic reticulum (ER) due to the presence of a signal sequence which is cleaved off by the enzyme signal peptidase located in the rough ER membrane. The protein is then transported from the ER to the Golgi and via Golgi derived secretory vesicles to the cell surface (S. Pfeffer and J. Rothman, Ann. Rev. Biochem. 56:829–52, 1987). Another major step in the production of correctly processed and correctly folded proteins is the conversion of proproteins to the mature forms in the Golgi apparatus and secretory vesicles. The cleavage of the proprotein occurs at a so-called dibasic site, i.e. a motif consisting of at least two basic amino acids. The processing is catalysed by enzymes located in the Golgi-apparatus, the so-called "dibasic processing endoproteases".

There are different "dibasic processing endoproteases" known which are involved in the processing of protein precursors, for example the mammalian proteases furin, PC2, PC1 and PC3, and the product of the yeast YAP3 gene and yeast yscF (also named KEX2 gene product; herein referred to as KEX2p).

KEX2p is involved in the maturation of the yeast mating pheromone α-factor (J. Kurjan and I. Hershkowitz, Cell 30:933–943, 1982). The α-factor is produced as a 165 amino acid precursor which is processed during the transport to the cell surface. In the first step, the 19-amino acid signal sequence (pre-sequence) is cleaved off by the signal peptidase. Then the precursor is glycosylated and moves to the Golgi where a 66-amino acid pro-sequence is cut off by KEX2p. The α-factor pre-pro-sequence is also known as α-factor "leader" sequence. A second protease in the Golgi apparatus, i.e. the KEX1 gene product, is responsible for the final maturation of the protein.

KEX2p is encoded by the KEX2 gene and consists of a N-terminal catalytic domain, a Ser/Thr rich domain, a membrane-spanning domain and a C-terminal tail responsible for Golgi localization. Mutant KEX2p enzyme lacking 200 C-terminal amino acids, including the Ser/Thr rich domain, the membrane spanning domain and the C-terminal tail, still retains KEX2p protease function, viz. cleavage at the C-terminal side of a pair of basic amino acids, such as Lys-Arg or Arg-Arg [Fuller et al., 1989, Proc. Natl. Acad. Sci. 86, 1434–1438; Fuller et al., 1989, Science 246, 482–485].

Leader sequences such as the yeast α-factor leader sequence are widely used for the production of secreted heterologous proteins in eukaryotic cells. In many cases, however, great difficulties are encountered because considerable amounts of biologically inactive proteins are produced due to malfolding and aggregation of the proteins, especially in the case of low molecular weight proteins.

OBJECT OF THE INVENTION

Surprisingly, it has been found that a higher ratio of biologically active correctly folded heterologous protein to inactive malfolded protein is produced in the host cell if the host cell has a "dibasic processing endoprotease" activity in the endoplasmic reticulum (ER).

Thus, it is an object of the invention to provide a method for the preparation of heterologous biologically active protein comprising the use of a host cell having a "dibasic processing endoprotease" in the ER. Other objects are the provision of a host cell having a "dibasic processing endoprotease" variant which is located in the ER due to the transformation with a gene encoding the "dibasic processing endoprotease" variant, further the provision of a DNA molecule comprising such a gene, and the provision of methods for the preparation of such a DNA molecule and of such a host cell.

DETAILED DESCRIPTION OF THE INVENTION

Process for the Preparation of Heterologous Protein

The invention concerns a process for the preparation of heterologous biologically active protein liberated in the host cell from a proprotein, said process comprising the use of a host cell having a "dibasic processing endoprotease" activity in the ER.

A "dibasic processing endoprotease" activity within the meaning of the present invention is the activity of an endoprotease specific for a motif of two basic amino acids, e.g. Arg-Arg, Arg-Lys, Lys-Arg or Lys-Lys, which endoprotease is naturally located in the Golgi apparatus and is naturally involved in the processing of proproteins or polyproteins.

The term "dibasic processing endoprotease" includes eukaryotic enzymes such as of mammalian origin, e.g. furin, PC2, PC1, PC3 (Barr, Cell 66:1–3, 1991), and preferentially enzymes derived from yeast, such as the YAP3 endoprotease [Egel-Mitani et at., Yeast 6: 127–137(1990)] and, most preferentially the S. cerevisiae endoprotease KEX2p.

The biologically active variants of the "dibasic processing endoprotease" of the invention are not restricted to the Golgi apparatus but are located in the ER due to the presence of an ER retention signal, i.e. a structure which is suitable for the retention of a "dibasic processing endoprotease" in the ER. The naturally occurring "dibasic processing endoproteases" are attached to the membrane of the Golgi apparatus or secretory vesicles due to a membrane anchor, i.e. a hydrophobic mambrane-spanning sequence. The ER retention signals are to be linked to the C-terminus of the protein, i.e. the "dibasic processing endoprotease" in order to locate the protease in the ER. Such a fusion protein consists of a protease and an ER retention signal is hereinafter called "ER-located dibasic processing endoprotease".

In a preferred embodiment of the invention the ER retention signal is attached to the C-terminus of a soluble form of a "dibasic processing endoprotease", i.e. a variant of a "dibasic processing endoprotease" which is not attached to a cell membrane. Such a soluble form lacks the hydrophobic membrane spanning sequence but still retains the typical enzymatic "dibasic processing" function.

A preferred example of a soluble "dibasic processing endoprotease" useful in the present invention is a soluble *S. cerevisiae* KEX2p, i.e. a KEX2p variant lacking the hyrophobic membrane-spanning sequence located in the region $Tyr^{679}$ to $Met^{699}$ [the amino acid sequence of the 814-residue *S. cerevisiae* KEX2p is known from K. Mizuno et al., Biochem. Biophys. Res. Commun. 156, 246–254 (1988)]. In particular, in a soluble KEX2p endoprotease according to the invention, the membrane binding site has selectively been removed. Hence the C-terminus starting with, for example, amino acid 700 (Lys) is still present, or the whole C-terminus including the membrane binding site, i.e. 136 to approximately 200 amino acids from the C-terminus, has been removed. Such soluble KEX2p proteins are described, for example, in EP 327,377 or in R. S. Fuller et al., Proc. Natl. Acad. Sci. USA 86, 1434–1438 (1989). The most preferred soluble "dibasic processing endoprotease" of the invention is the soluble KEX2p having the sequence depicted in the sequence listing under SEQ ID No. 1 and is hereinafter referred to as $KEX2p_s$.

An ER-retention signal is a structure determining the location of a polypeptide in the ER. The location in the ER may be based on a specific attachment to the ER membrane or preferentially on the prevention of the transport of a soluble protein into the Golgi apparatus by retransportation of the polypeptide from a compartment between the Golgi apparatus and the ER into the ER lumen. ER retention signals used preferentially in the present invention are of the latter type, i.e. such preventing the transport of soluble protein to the Golgi apparatus.

A preferred example of such an ER retention signal is the so-called KDEL sequence (SEQ ID No. 3) functional in mammalian cells. More preferred is the DDEL sequence (SEQ ID No. 4) functional in the yeast *Kluyveromyces lactis* and most preferred is the HDEL sequence (SEQ ID No. 2) functional in *S. cerevisiae* and in *K. lactis*.

Preferred forms of the "ER-located dibasic processing endoprotease" comprise the ER-retention signal KDEL sequence attached to a "dibasic processing endoprotease" of a mammalian cell such as, for example, furin, PC1, PC2 or PC3 (P. J. Barr, supra), or preferably to a soluble variant thereof, or also to a *S. cerevisiae* KEX2p, which latter is known to be functional in mammalian cells, or preferably to a soluble variant thereof. If such an "ER-located dibasic processing endoprotease", e.g. furinKDEL, PC1KDEL, PC2KDEL, PC3KDEL, or KEX2pKDEL enzymes, are produced in a mammalian host cell transformed with a gene for the expression of a heterologous protein, a higher proportion of correctly folded, secreted heterologous protein is produced.

More preferably, the DDEL retention signal is fused to a *K. lactis* KEX2p analog or preferably to a soluble variant thereof, or to a *S. cerevisiae* KEX2p or preferably to a soluble variant thereof, in particular to $KEX2p_s$. *S. cerevisiae* KEX2p is functional also in *K. lactis*. Such a KEX2pDDEL produced in a *K. lactis* host cell allows the expression of a higher proportion of correctly folded, secreted heterologous protein.

Most preferably, the HDEL retention signal is fused to a *S. cerevisiae* KEX2p, or preferably to a soluble variant thereof, in particular to $KEX2p_s$. Such a KEX2pHDEL protein produced in a *K. lactis* or, more preferably, in a *S. cerevisiae* host cell allows the expression of a higher proportion of correctly folded, secreted heterologous protein.

In order to produce a host cell in which an "ER-located dibasic processing endoprotease" is produced, the host cell must be transformed with an expression cassette encoding an "ER-located dibasic processing endoprotease". The host cell which is transformed may still contain an intact endogeneous gene for the endogeneous dibasic processing endoprotease on the chromosome, i.e. in the case of the *S. cerevisiae* system the host cell which is to be transformed with KEX2pHDEL may be a $KEX2^+$ cell, e.g. strain AB110. However, gene coding for the corresponding endogeneous dibasic processing endoprotease may also be destroyed, i.e. in the case of the *S. cerevisiae* system the host cell may be a $kex2^-$ cell, e.g. strain AB110 $kex2^{31}$.

For the transformation of a host cell hybrid vectors are used which provide for replication and expression of an expression cassette encoding the "ER-located dibasic processing endoprotease". These hybrid vectors may be extrachromosomally maintained vectors or also vectors which are integrated into the host genome so that a cell is produced which is stably transformed with a said expression cassette. Suitable extrachromosomally maintained vectors and also vectors integrating in to the host genome the transformation of mammalian cells or of yeast cells are well known in the art.

The hybrid vectors may be derived from any vector useful in the art of genetic engineering, such as from viruses, plasmids or chromosomal DNA, such as derivatives of SV40, Herpes-viruses, Papilloma viruses, Retroviruses, Baculovirus, or derivatives of yeast plasmids, e.g. yeast 2μ plasmid.

Several possible vector systems are available for integration and expression of the cloned DNA of the invention. In principle, all vectors which replicate and/or express a desired polypeptide gene comprised in an expression cassette of the invention in the chosen host are suitable. The vector is selected depending on the host cells envisaged for transformation. Such host cells are preferably mammalian cells (if a "dibasic processing endoprotease" functional in mammalian cells is used) or, more preferably, yeast cells (if a "dibasic processing endoprotease" functional in yeast cells is used). In principle, the extrachromosomally maintained hybrid vectors of the invention comprise the expression cassette for the expression of an ER-located "dibasic processing endoprotease", and an origin of replication or an autonomously replicating sequence.

An origin of replication or an autonomously replicating sequence (a DNA element which confers autonomously replicating capabilities to extrachromosomal elements) is provided either by construction of the vector to include an exogenous origin such as, in the case of the mammalian vector, derived from Simian virus (SV 40) or another vital source, or by the host cell chromosomal mechanisms.

A hybrid vector of the invention may contain selective markers depending on the host which is to be transformed, selected and cloned. Any marker gene can be used which facilitates the selection of transformants due to the phenotypic expression of the marker. Suitable markers are particularly those expressing antibiotic resistance, e.g. against tetracycline or ampicillin, or genes which complement host lesions. It is also possible to employ as markers structural genes which are associated with an autonomously replicating segment providing that the host to be transformed is auxotrophic for the product expressed by the marker.

Preferred vectors suitable for the preparation of hybrid vectors of the invention, i.e. comprising an expression cassette for the preparation of an ER-located "dibasic processing endoprotease" are those which are suitable for replication and expression in *S. cerevisiae* and contain a yeast-replication origin and a selective genetic marker for yeast. Hybrid vectors that contain a yeast replication origin, for example the chromosomal autonomously replicating segment (ARS), are retained extrachromosomally within the yeast cell after transformation and are replicated autonomously during mitosis. Also, hybrid vectors that contain sequences homologous to the yeast 2μ plasmid DNA or that contain ARS and a sequence of a chromosomal centromere, for example CEN4, can be used. Preferred are the 2μ based plasmids containing the complete or partial *S. cerevisiae* 2μ plasmid sequence. Suitable marker genes for yeast are especially those that impart antibiotic resistance to the host or, in the case of auxotrophic yeast mutants, genes that complement the host lesions. Corresponding genes impart, for example, resistance to the antibiotic cycloheximide or provide for prototrophy in an auxotrophic yeast mutant, for example the URA3, LEU2, HIS3 or the TRP1 gene.

Preferably, hybrid vectors furthermore contain a replication origin and a marker gene for a bacterial host, especially *E. coli*, so that the construction and the cloning of the hybrid vectors and their precursors can be carried out in *E. coli*.

In a most preferred embodiment of the invention a kex2⁻ strain of *S. cerevisiae* is transformed either with an extrachromosomally maintained plasmid or with integration plasmid comprising an expression cassette for the expression of a soluble KEX2pHDEL.

An "expression cassette" for the expression of an ER-located "dibasic processing endoprotease" means a DNA sequence capable of expressing such a polypeptide and comprises a promoter and a structural gene and, if desired, a transcriptional terminator and optionally a transcriptional enhancer, ribosomal binding site and/or further regulatory sequences.

Such an expression cassette may contain either the regulatory elements naturally linked with the corresponding "dibasic processing endoprotease" gene, heterologous regulatory elements or a mixture of both, i.e., for example, a homologous promoter and a heterologous terminator region.

A wide variety of promoter sequences may be employed, depending on the nature of the host cell. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of viral or eukaryotic cDNAs, e.g. from the expression host.

Examples for promoters are as above, i.e. yeast TRP1-, ADHI-, ADHII-, CYC1, GAL1/10, CUP1, PHO3-, or PHO5-promoter, or promoters from heat shock proteins ,or glycolytic promoters such as glyceraldehyde-3-phosphate dehydrogenase (GAP) promoter (including 5' truncated GAP) or a promoter of the enolase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, furthermore α-factor promoter and hybrid promoters, such as hybrid PHO5-GAP or ADH2-GAP promoters or hybrid promoters using heat shock elements.

Promoters suitable for the expression in mammalian cells are, for example, derived from viruses, e.g. SV40, Rous sarcoma virus, adenovirus 2, bovine papilloma virus, papovavirus, cytomegalovirus derived promoters, or are mammalian cell derived promoters, e.g. of the actin, collagen, myosin, or β-globin gene. The yeast promoters may be combined with enhancing sequences such as the yeast upstream activating sequences (UAS) and the promoters active in mammalian cells may be combined with vital or cellular enhancers such as the cytomegalovirus IE enhancers, SV40 enhancer, immunoglobulin gene enhancer or others.

Enhancers are transcription-stimulating DNA sequences, e.g. derived from viruses such as Simian virus, polyoma virus, bovine papilloma virus or Moloney sarcoma virus, or of genomic origin. An enhancer sequence may also be derived from the extrachromosomal ribosomal DNA of *Physarum polycephalum*, or it may be the upstream activation site from the yeast acid phosphatase PHO5 gene, or the yeast PHO5, TRP, PHO5-GAPDH hybrid, or the like promoter.

A host cell of the invention having a "dibasic processing endoprotease" activity in the ER is useful for the preparation of correctly processed heterologous proteins. For this purpose an expression cassette for the expression of a gene encoding the desired heterologous protein is of course also to be introduced into the host cell. Such an expression cassette is herein named "production gene".

Such a production gene comprises a promoter region, a DNA sequence encoding signal peptide which can be cleaved off by a signal peptidase, a DNA sequence encoding a pro-sequence which can be cleaved off from the desired heterologous gene product by a "dibasic processing endoprotease", a DNA sequence encoding a desired heterologous gene product and/or a transcriptional terminator region and optionally a transcriptional enhancer, ribosomal binding site and/or further regulatory sequences. The coding regions for signal peptide, the pro-sequence and the heterologous protein are attached "in frame", i.e. the signal peptide is after the translation of the structural gene covalently linked to the N-terminus of the pro-sequence and the latter is after the translation of the gene covalently linked to the N-terminus of the heterologous protein.

The pro-sequence can be any sequence from a random genomic library of fragments which can act as a molecular chaperone, i.e. a polypeptide which in cis or in trans can influence the formation of an appropriate conformation. Preferably, it is a random sequence which allows membrane translocation. In particular preferred is the α-factor prosequence.

As in the expression cassette described above for the expression of a "dibasic processing endoprotease", a wide variety of regulator sequences may be employed, depending on the nature of the host cell. For example, promoters that are strong and at the same time well regulated are the most useful. Sequences for the initiation of translation are for example Shine-Dalgarno sequences. Sequences necessary for the initiation and termination of transcription and for stabilizing the mRNA are commonly available from the noncoding 5'-regions and 3'-regions, respectively, of vital or eukaryotic cDNAs, e.g. from the expression host.

Signal peptides within the meaning of the present invention are presequences directing the translocation of the desired polypeptide to the ER, for example the α-factor signal sequence. Further signal sequences are known from literature, e.g. those compiled in von Heijne, G., Nucleic Acids Res. 14, 4683 (1986).

Examples for suitable promoters are as above, i.e. yeast TRP1-, ADHI-, ADHII-, CYC1, GAL1/10, CUP1, PHO3-, or PHO5-promoter, or promoters from heat shock proteins, or glycolytic promoters such as glyceraldehyde-3-phosphate dehydrogenase (GAP) promoter (including 5' truncated GAP) or a promoter of the enolase, 3-phosphoglycerate kinase (PGK), hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase genes, furthermore α-factor promoter and hybrid promoters, such as hybrid PHO5-GAP or ADH2-GAP promoters or hybrid promoters using heat shock elements, or promoters derived from eukaryotic viruses, e.g. SV40, Rous sarcoma virus, adenovirus 2, bovine papilloma virus, papovavirus, cytomegalovirus derived promoters or mammalian cell derived promoters, e.g. of the actin, collagen, myosin, or β-globin gene. The eukaryotic promoters may be combined with enhancing sequences such as the yeast upstream activating sequences (UAS) or viral or cellular enhancers such as the cytomegalovirus IE enhancers, SV40 enhancer, immunoglobulin gene enhancer or others.

The expression cassette encoding the ER-located "dibasic processing endoprotease" and the production gene may comprise promoters of the same or of different types. For example, they may both be regulated by an inducible promoter which allows the concerted expression of the precursor of the heterologous protein and of the ER-located "dibasic processing endoprotease" processing it.

In a preferred embodiment of the invention a production gene suitable for the expression in a *S. cerevisiae* cell which cell contains an ER-located "dibasic processing endoprotease", prefeably YAP3pHDEL, more preferably KEX2pHDEL or, most preferably, KEX2p$_s$HDEL, comprises a structural fusion gene composed of a DNA sequence encoding a yeast pro-sequence which can be cleaved off from the precursor by a yeast "dibasic processing endoprotease", preferably the *S. cerevisiae* α-factor leader sequence and downstream a DNA sequence coding for a desired heterologous protein, said fusion gene being under the control of expression control sequences regulating transcription and translation in yeast.

The heterologous protein may be any protein of biological interest and of prokaryotic or especially eukaryotic, in particular higher eukaryotic such as mammalian (including animal and human), origin and is, for example, an enzyme which can be used, for example, for the production of nutrients and for performing enzymatic reactions in chemistry or molecular biology, or a protein which is useful and valuable for the treatment of human and animal diseases or for the prevention thereof, for example a hormone, polypeptide with immunomodulatory, anti-viral and anti-tumor properties, an antibody, viral antigen, blood clotting factor, a fibrinolytic agent, a growth regulation factor, furthermore a foodstuff and the like.

Example of such proteins are e.g. hormones such as secretin, thymosin, relaxin, calcitonin, luteinizing hormone, parathyroid hormone, adrenocorticotropin, melanocyte-stimulating hormone, β-lipotropin, urogastrone, insulin, growth factors, such as epidermal growth factor (EGF), insulin-like growth factor (IGF), e.g. IGF-1 and IGF-2, mast cell growth factor, nerve growth factor, glia derived nerve cell growth factor, platelet derived growth factor (PDGF), or transforming growth factor (TGF), such as TGFβ, growth hormones, such as human or bovine growth hormones, interleukin, such as interleukin-1 or -2, human macrophage migration inhibitory factor (MIF), interferons, such as human α-interferon, for example interferon-αA, αB, αD or αF,β-interferon, γ-interferon or a hybrid interferon, for example an αA-αD- or an αB-αD-hybrid interferon, especially the hybrid interferon BDBB, proteinase inhibitors such as α$_1$-antitrypsin, SLPI and the like, hepatitis virus antigens, such as hepatitis B virus surface or core antigen or hepatitis A virus antigen, or hepatitis nonA-nonB antigen, plasminogen activators, such as tissue plasminogen activator or urokinase, hybrid plasminogen activators, such as K$_2$tuPA, tick anticoagulant peptide (TAP), tumour necrosis factor, somatostatin, renin, immunoglobulins, such as the light and/or heavy chains of immunoglobulin D, E or G, or human-mouse hybrid immunoglobulins, immunoglobulin binding factors, such as immunoglobulin E binding factor, human calcitonin-related peptide, blood clotting factors, such as factor IX or VIIIc, platelet factor 4, erythropoietin, eglin, such as eglin C, desulfatohirudin, such as desulfatohirudin variant HV1, HV2 or PA, corticostatin, echistatin, cystatins, human superoxide dismutase, viral thymidin kinase, β-lactamase or glucose isomerase. Preferred are human α-interferon e.g. interferon αB, or hybrid interferon, particularly hybrid interferon BDBB (see EP 205,404), human tissue plasminogen activator (t-PA), human single chain urokinase-type plasminogen activator (scu-PA), hybrid plasminogen activator K$_2$tuPA (see EP 277,313), human calcitonin, desulfatohirudin, e.g. variant HV1, even more preferred insulin-related proteins such as insulin, relaxin, the even more preferred insulin-like growth factor II and, in particular, insulin-like growth factor I. Proteins containing a pair of basic amino acids, such as Arg-Arg, Lys-Arg, Lys-Lys and Arg-Lys, exposed on the protein surface and therefore amenable to proteolytic cleavage, are not suited for the process according to the invention and will have to be mutated such that one of the consecutive basic amino acids is replaced by another non-basic amino acid without affecting the biological activity.

A production gene needs not necessarily be located on the same vector molecule as the gene encoding the ER-located "dibasic processing endoprotease". In the case the latter is located on a vector which is extrachromosomally maintained, it may, be advantageous if the production gene is located on the same vector molecule.

Expression vectors suitable for the expression of a production gene are, for example, also those which are described above as being suitable for the expression of an ER-located "dibasic processing endoprotease", i.e. vectors derived from any vector useful in the art of genetic engineering, such as from viruses, plasmids or chromosomal DNA, such as derivatives of SV40, Herpes-viruses, Papilloma viruses, Retroviruses, Baculovirus, or derivatives of yeast plasmids, e.g. yeast 2μ plasmid. Preferred are vectors for replication and expression in *S. cerevisiae*.

Preferably, the hybrid vectors of the present invention also contain a replication origin and a marker gene for a bacterial host, especially *E. coli*, so that the construction and the cloning of the hybrid vectors and their precursors can be carried out in *E. coli*.

A process for the preparation of heterologous biologically active protein comprising the use of a host cell having a "dibasic processing endoprotease" activity in the ER according to the invention comprises (a) transforming a suitable host cell with a hybrid vector comprising an expression cassette encoding an ER-located "dibasic processing endoprotease" and with a hybrid vector encoding a production gene, or (b) transforming a suitable host cell with a hybrid vector comprising both an expression cassette encoding an ER-located "dibasic processing endoprotease" and a production gene, or (c) transforming a suitable host cell which is stably transformed with a gene encoding an ER-located "dibasic processing endoprotease" with a hybrid vector encoding a production gene, culturing the transformed host cells under conditions in which the gene encoding the ER-located "dibasic processing endoprotease" and the production gene are expressed, and isolating the desired heterologous polypeptide from the culture medium according to conventional methods.

The invention preferentially concerns a process wherein a yeast strain, more preferably a *Saccharomyces cerevisiae* strain, e.g. AB110 or AB110 kex2⁻, an ER-located yeast "dibasic processing endoprotease", e.g. YAP3DDEL or, preferably, YAP3HDEL or, more preferably, KEX2pHDEL, most preferably KEX2p$_s$HDEL, is used for the preparation of an insulin-like protein, preferably IGF-2 and, more preferably, IGF-1, which is produced as a precursor containing the α-factor leader sequence.

The transformation is accomplished by methods known in the art, for example, according to the method described by Hinnen et al [Proc. Natl. Acad. Sci. USA 75, 1919(1978)]. This method can be divided into three steps:

(1) Removal of the yeast cell wall or parts thereof.
(2) Treatment of the "naked" yeast cells (spheroplasts) with the expression vector in the presence of PEG (polyethyleneglycol) and $Ca^{2+}$ ions.
(3) Regeneration of the cell wall and selection of the transformed cells in a solid layer of agar.

The transformed host cells are cultured by methods known in the art in a liquid medium containing assimilable sources of carbon, nitrogen and inorganic salts. Various sources of carbon can be used for culture of the transformed yeast cells according to the invention. Examples of preferred sources of carbon are assimilable carbohydrates, such as glucose, maltose, mannitol or lactose, or an acetate, which can be used either by itself or in suitable mixtures. Examples of suitable sources of nitrogen are amino acids, such as casaminoacids, peptides and proteins and their degradation products, such as tryptone, peptone or meat extracts, yeast extracts, malt extract and also ammonium salts, for example ammonium chloride, sulfate or nitrate, which can be used either by themselves or in suitable mixtures. Inorganic salts which can also be used are, for example, sulfates, chlorides, phosphates and carbonates of sodium, potassium, magnesium and calcium. The medium furthermore contains, for example, growth-promoting substances, such as trace elements, for example iron, zinc, manganese and the like, and preferably substances which exert a selection pressure and prevent the growth of cells which have lost the expression plasmid. Thus, for example, if a yeast strain which is auxotrophic in, for example, an essential amino acid, is used as the host microorganism, the plasmid preferably contains a gene coding for an enzyme which complements the host defect. Cultivation of the yeast strain is performed in a minimal medium deficient in said amino acid.

Culturing is effected by processes which are known in the art. The culture conditions, such as temperature, pH value of the medium and fermentation time, are chosen such that a maximum titre of the heterologous proteins prepared according to the invention is obtained. Thus, the yeast strain is preferably cultured under aerobic conditions by submerged culture with shaking or stirring at a temperature of about 20° to 40° C., preferably about 30° C., and a pH value of 5 to 8, preferably at about pH 7, for about 4 to about 96 hours, preferably until maximum yields of the proteins of the invention are reached. The culture medium is selected in such a way that selection pressure is exerted and only those cells survive which still contain the hybrid vector DNA including the genetic marker. Thus, for example, an antibiotic is added to the medium when the hybrid vector includes the corresponding antibiotic resistance gene.

When the cell density has reached a sufficient value culturing is interrupted and the medium containing the product is separated from the cells which can be provided with fresh medium and used for continuous production. The protein can also accumulate within the cells, especially in the periplasmic space. In the latter case the first step for the recovery of the desired protein consists in liberating the protein from the cell interior. The cell wall is first removed by enzymatic digestion with glucosidases or, alteratively, the cell wall is removed by treatment with chemical agents, i.e. thiol reagents or EDTA, which give rise to cell wall damages permitting the produced protein to be released. The resulting mixture is enriched for heterologous protein by conventional means, such as removal of most of the non-proteinaceous material by treatment with polyethyleneimine, precipitation of the proteins using ammonium sulphate, gel electrophoresis, dialysis, chromatography, for example, ion exchange chromatography (especially preferred when the heterologous protein includes a large number of acidic or basic amino acids), size-exclusion chromatography, HPLC or reverse phase HPLC, molecular sizing on a suitable Sephadex® column, or the like. The final purification of the pre-purified product is achieved, for example, by means of affinity chromatography, for example antibody affinity chromatography, especially monoclonal antibody affinity chromatography using antibodies fixed on an insoluble matrix by methods known in the art.

RECOMBINANT DNA MOLECULES

The invention also concerns a recombinant DNA molecule encoding an expression cassette for an ER-located "dibasic processing endoprotease" as defined above. The invention further concerns hybrid vectors comprising such a recombinant DNA molecule.

The present invention preferably concerns a recombinant DNA molecule or hybrid vector comprising the coding region for KEX2p, preferentially for a soluble KEX2p variant, most preferably for KEX2p$_s$ shown in the sequence listing under SEQ ID No. 1, and for an ER retention signal, preferentially for the HDEL sequence shown in the sequence listing under SEQ ID No. 2. The coding sequence for the ER retention signal is preferentially located in downstream direction of the KEX2p coding region. A KEX2p with HDEL attached at the C-terminus is herein named KEX2pHDEL, the corresponding structural gene is KEX2HDEL.

As mentioned above some soluble KEX2p variants are known from the literature. Further deletion mutants according to the invention can be prepared using methods known in the art, for example by preparing a corresponding DNA coding for said mutant, inserting it in a suitable vector DNA under the control of an expression control sequence, transforming suitable host microorganisms with the expression vector formed, culturing the transformed host microorganism in a suitable culture medium and isolating the produced mutant. The DNA coding for any of said mutants can be produced for example, by taking a plasmid containing the DNA coding for KEX2p and (1) digesting it with a restriction enzyme which cleaves within or 3' of the DNA region coding for the membrane binding site (for example, EcoRI, BstXI or NarI), digesting the cleaved DNA with a suitable endonuclease, for example Bal31, such that said DNA region is removed and recircularizing the linearized plasmid by blunt end ligation or the like, or (2) choosing or creating (for example by site-directed mutagenesis) one restriction site 5' to and one restriction site 3' to the DNA region coding for the membrane binding site (for example PvuII and NarI or EcoRI; the 3' restriction site may also be located within the plasmid DNA adjacent to the translation stop signal of the KEX2 gene), digesting the plasmid with two restriction enzymes recognizing said restricting sites and recircularizing the linearized plasmid by blunt end ligation or the like, or (3) deleting the DNA region coding for the membrane binding site by using loop-out mutagenesis, or (4) totally deleting the C-terminus by digesting with PvuII in the case of KEX2 and recircularizing the linearized plasmid by blunt end ligation or the like. As the DNA sequences of KEX2 are known (K. Mizumo et al. supra) a suitable mutagenic oligonucleotide can easily be devised and used to delete said DNA region applying the M13 cloning system. Care must be taken that the mutated KEX2 genes are linked with a DNA sequence encoding a yeast ER retention signal. Such a DNA sequence can be introduced at the desired place via a synthetic linker DNA or it may be provided by the adjacent vector DNA. Preferentially, the mutated KEX2 genes include at their 3' ends codons which code for the HDEL sequence defined above. All of these methods make use of conventional techniques.

Within the scope of the present invention are also recombinant DNA molecules comprising DNA sequences which are degenerate within the meaning of the genetic code to the DNA sequences with SEQ ID Nos. 1 and 2, i.e. DNA sequences encoding the same amino acid sequences although nucleotides are exchanged. Such degenerate DNA sequences may, for example, contain new restriction enzyme cleavage sites.

HOST STRAINS

Another aspect of the present invention involves host cells, preferably mammalian, more preferably yeast, even more preferably *K. lactis* and most preferably *S. cerevisiae* cells transformed with a hybrid vector of the invention comprising an expression cassette encoding an ER-located "dibasic processing endoprotease". The invention also concerns host cells which are stably transformed with an expression cassette encoding an ER-located "dibasic processing endoprotease", i.e. which comprise such a recombinant expression cassette integrated into a chromosome.

Suitable hosts for the integration of an expression cassette encoding KEX2HDEL are e.g. kex2⁻ mutants of yeast, preferentially of *S. cerevisiae*. The method for the preparation of transformed host cells comprises transforming host cells with an integration vector consisting of a KEX2pHDEL expression cassette which is under the control of any constitutive or inducible promoter, preferably of the promoters defined above or of the promoter of the KEX2 gene, and selecting stably transformed cells. Stable integrative transformation is state of the art and can be performed, for example, according to the procedued reported for mammalian cells in P. L. Felgner et al., Proc. Natl. Acad. Sci USA 84:7413–7417(1987) or in F. L. Graham et al., Virology 52:456–467(1973) and for *S. cerevisiae* cells in R. Rothstein, Methods Enzymol. 194:281–302(1991).

The invention concerns especially the recombinant DNA molecules, the hybrid vectors, the transformed hosts, the proteins and the methods for the preparation thereof and the method for the preparation of a biologically active protein as described in the examples.

The following examples serve to illustrate the invention but should not be construed as a limitation thereof.

EXAMPLE 1

Construction of a Shortened KEX2 Gene Encoding Soluble KEX2p Variant

In order to get a soluble KEX2p protease activity, a mutant KEX2 gene lacking 600 bp, coding for the C terminal 200 amino acids, is constructed. The truncated gene is under the control of the KEX2 promoter reaching from −1 to −502. Translation is terminated at a stop codon (TAA) originating from the polylinker of pUC18.

In detail, plasmid pUC19 [Boehringer Mannheim GmbH, FRG] is digested to completion with HindIII and the 2686 bp fragment is isolated. The ends are filled in and the fragment is religated. An aliquot of the ligation mixture is added to calcium-treated, transformation competent *E. coli* JM101 [Invitrogen, San Diego, USA] cells. 12 transformed ampicillin resistant *E. coli* transformants are grown in the presence of 100 µg/ml ampicillin. Plasmid DNA is prepared and analysed by digestion with HindIII as well as with BamHI. The plasmid lacking the HindIII site is designated pUC19woH.

A 3207 bp BalI-AhaIII KEX2 fragment (obtainable from total genomic yeast DNA) is provided at both ends with BamHI linkers followed by a complete digestion with BamHI. Plasmid pUC19woH is cut to completion with BamHI, the linear 2690 bp fragment is isolated and ligated to the BamHI KEX2 fragment described above. An aliquot of the ligation mixture is transformed into *E. coli* JM101 cells. 12 transformed, ampicillin resistant colonies are grown in ampicillin (100 µg/ml) containing LB medium, plasmid DNA is extracted and analyzed by BamHI digests. One clone with the expected restriction fragments is selected and called pKS301b (deposited as DSM 6028).

The 2 µm yeast vector pAB24 which corresponds essentially to plasmid pDP34 (deposited as DSM 4473) is cut to completion with BamHI and the linear pAB24 fragment is isolated. Plasmid pKS301b is digested with BamHI and the fragment containing the complete KEX2 gene is isolated and ligated to the linearized yeast vector pAB24.An aliquot of the ligation mixture is transformed into *E. coli* JM101 and plasmid DNA of twelve positive clones is examined by BamHI digests. One clone with the expected restriction fragments is referred to as pAB226.

Plasmid pKS301b is digested to completion with SphI, PvuII and ScaI. The 2.37 kb SphI-PvuII fragment containing KEX2 sequences from −502 to +1843 and a part of the pUC19 polylinker is isolated. Plasmid pUC18 [Boehringer Mannheim, FRG] is cut to completion with SphI and SmaI. The 2660 bp SphI-SmaI pUC18 fragment is ligated to the 2.37 kb SphI-PvuII KEX2 fragment by SphI/SphI and PvuII/SmaI ligation. The PvuII/SmaI ligation results in the fusion of the KEX2 ORF coding for 614 amino acids to an ORF in the pUC18 sequences which codes for 7 additional C-terminal amino acids (—G—V—P—S—S—N—S) and is followed by a stop codon (TAA). An aliquot of the ligation mixture is transformed into *E. coli* JM101. Plasmid DNA is isolated from ampicillin resistant *E. coli* transformants and analyzed by digestion with SphI and EcoRI as well as with HindIII. One clone with the expected restriction pattern is referred to as p18kexp. In the sequence listing under SEQ ID No. 1 the ORF encoding the soluble KEX2p$_s$ with KEX2-derived DNA is shown.

Plasmid p18kexp is cut to completion with PvuII, and ScaI. The 2552 bp SalI-PvuII fragment containing the KEX2 sequences reaching from −502 to +1843 as well as 206 bp of pUC18 sequences is isolated. Plasmid pDP34 is digested with BamHI and the ends of the linearized plasmid are filled in. After inactivation of T4 polymerase the linearized filled-in plasmid is cut with SalI and the 11.78 kb fragment is isolated. The pDP34 BamHI*-SalI fragment (BamHI*: filled-in BamHI) is ligated to the 2552 bp SalI-PvuII fragment by SalI/SalI and BamHI*/PvuII ligation. An aliquot of the ligation mixture is transformed into transformation competent E. coli JM101 cells. Plasmid DNA is extracted from ampicillin resistant cells and analyzed by restriction analysis with SalI, NcoI, SmaI, XbaI, EcoRI. One clone with the expected restriction fragments is referred to as pDPkexp.

EXAMPLE 2

Construction of pDPkexpHDEL

Plasmid p18kexp (see example 1) consists of the truncated KEX2 gene coding for soluble KEX2p (KEX2p$_s$) inserted into the polylinker region of pUC18. The DNA sequence coding for the C-terminal end of KEX2p$_s$ in p18kexp is followed by an Asp718 and an EcoRI site (see SEQ ID No. 1). The plasmid is cut with Asp718 and EcoRI and is ligated with the hybridized oligonucleotides with SEQ ID Nos. 11 and 12, encoding the HDEL sequence and two stop codons, resulting in the ligation product p18kexpHDEL. Plasmids p18kexp and p18kexpHDEL can be distinguished by SacI or SfuI digestion. The polylinker insertion region was squenced in p18kexpHDEL.

Plasmid p18kexpHDEL was cut with SalI, PvuII and ScaI and the 2572 bp SalI-PvuII fragment was isolated.

Plasmid pDP34 was cut with BamHI and the sticky ends were filled in with Klenow polymerase. After filling in, the polymerase was destroyed by phenol/chlorophorm and chlorophorm extractions followed by an ethanol precipitation. The BamHI cut filled in pDP34 fragment was then digested with SalI and the 11780 bp SalI-BamHI* (BamHI*: filled in BamHI site) was isolated.

The 2572 SalI-PvuII fragment isolated from p18kexpHDEL was ligated with the 11780 bp SalI-BamHI* pDP34 fragment. Ligation of SalI/SalI and PvuII/BamHI* led to the plasmid pDPkexpHDEL.

EXAMPLE 3

Construction of an Yeast Vector Containing the IGF-1 Expression Cassette

Plasmid pDP34 is an E. coli - S. cerevisiae shuttle vector containing the complete 2μ sequence, the yeast genomic URA3 and d LEU2 sequences as selectable markers for yeast, and pBR322 sequences for selection and propagation in E. coli [A. Hinnen, B. Meyhack and J. Heim, in Yeast Genetic Engineering (P. J. Barr, A. J. Brake & P. Valenzuela, eds., pp. 193–213 (1989), Butterworth Publishers, Stoneham]. A 276 bp SalI-BamHI fragment of pBR322 [Boehringer Mannheim GmbH, Germany] is ligated to the isolated linear vector after digestion with SalI and BamHI. An aliquot of the ligation mixture is added to calcium-treated transformation competent E. coli HB101 cells [Invitrogen, San Diego, USA]. Four transformed ampicillin resistant E. coli transformants are grown in the presence of 100 μg/ml ampicillin. Plasmid DNA is prepared and analysed by digestion with SalI-BamHI. One plasmid having the expected restriction fragments is referred to as pDP34A. The human insulin-like growth factor-1 (IGF-1) gene expression cassette, for expression in yeast, is ligated into the BamHI site of pDP34A. The DNA sequence of the expression cassette,

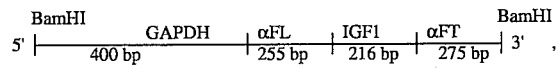

is shown under SEQ ID No. 5. It consists of a BamHI-cleavable linker, followed by an about 400 bp fragment of the S. cerevisiae glyceraldehyde-3-phosphate dehydrogenase (GAPDH) promoter, then the S. cerevisiae α-factor leader sequence encoding the first 85 amino acids of the α-factor precursor (J. Kurjan et al., Cell 30:933–943, 1982), directly followed by a chemically synthesized IGF-1 gene [G. T. Mullenbach, A. L. Choo, M. S. Urdea, P. J. Barr, J. P. Merryweather, A. J. Brake, and P. Valenzuela, Fed. Proc. 42, 434 (abstr.) (1983)], the about 275 bp S. cerevisiae α-factor terminator (αFT; Kurian et al., Cell 30:933–943, 1982) and a second BamHI-cleavable linker. An aliquot of the ligation mixture is transformed in E. coli HB101. Plasmid DNA from 6 independent transformants is analysed with SalI as well as BamHI. One clone with the promoter of the expression cassette oriented 3' to the SalI-BamHI fragment is named pDP34A/GAPDH-αFL-IGF1-αFT.

EXAMPLE 4

Construction of Two Mutated α-Factor Leader Sequences

A 1146 bp BamHI fragment, consisting of the 400 bp GAPDH promoter, the 255 bp αFL sequence, the 216 bp chemically synthesized IGF-1 gene (IGF-1 gene and 2 stop codons) and the 275 bp αFT, released from pDP34A/GAPDH-αFL-IGF1-αFT (see example 3). It is ligated to BamHI digested, bacterial alkaline phosphatase (Gibco-BRL, Basel, Switzerland) treated replicative form (RF) of phage vector M13mp18 (Boehringer Mannheim GmbH, Germany). An aliquot of the ligation mixture is transformed in E. coli JM101. Plasmid DNA from 6 plaques is analysed with EcoRI, BamHI, and BamHI-SalI. One RF clone with the appropriate restriction fragments and with the promoter directly adjacent to the EcoRI site of the vector is selected and called mp18/BamHI/GAPDH-α FL-IGF1-αFT. Site-directed mutagenesis using the two-primer protocol [M. J. Zoller and M. Smith, Meth. in Enzymol. 154, 329–350 (1987)] employing the mutagenic oligodesoxyribonucleotide primer with SEQ ID No. 6 gives a new sequence of the αFL, changing the amino acids Ala° to Asp° and Pro$^{21}$ to Leu$^{21}$. Single-stranded DNA obtained from one positive clone after hybridization with the radioactively labelled mutagenic primer is sequenced [F. Sanger, S. Nicklen and A. R. Coulsen, Proc, Natl. Acad. Sci. U.S.A. 74, 5463–5467 (1977)] to confirm the desired mutations. The mutated αFL sequence is named αFLMut2 and the resultant phage is called mp18/BamHI/GAPDH-αFLMut2-IGF1 -αFT. Site-directed mutagenesis using the four mutagenic oligodesoxyribonucleotide primers with SEQ ID Nos. 7, 8, 9 and 10 yields an αFL sequence in which the following amino acids are exchanged:

Ala$^{13}$ to Asn$^{13}$, Gln$^{32}$ to Asn$^{32}$, Pro$^{34}$ to Thr$^{34}$, Gly$^{40}$ to Asm$^{40}$, Lys$^{76}$ to Asm$^{76}$, and Glu$^{78}$ to Thr$^{78}$.

DNA sequencing on single-stranded DNA template confirms all mutations.

The mutated αFL sequence is named αFLG1G2G3G5 and the phage is referred to as mp18/BamHI/GAPDH-αFLG1G2G3G5-IGF1-αFT.

EXAMPLE 5

Construction of Yeast Vectors Containing
GAPDH-αFL-IGF1-αFT,
GAPDH-αFLMut2-IGF1-αFT, and
GAPDH-αFLG1G2G3G5-IGF1-αFT To create an unique BglII site in the vector pDP34A (see example 3), plasmid DNA is digested to completion with SacI and the 3' overhang is flushed with T4 DNA polymerase (New England BioLabs, Beverly, Mass., USA). The linearized, blunt-ended vector pDP34A is ligated to BglII linkers (Boehringer Mannheim GmbH, Germany). After linker ligation, the vector DNA is digested with BglII and then religated. Plasmid DNA of 6 ampicillin resistant transformants, obtained after transformation of an aliquot of the religated mixture in *E. coli* HB101, is analysed with restriction enzymes BglII-SalI and BglII-ScaI. One clone with the expected restriction fragments, confirming the creation of a BglII site in place of the SacI site, is designated as pDP34B.

pDP34B is digested to completion with BamHI and is treated with bacterial alkaline phosphatase. This linearized vector DNA is used to subclone the 1146 bp BamHI fragments obtained from pDP34A/GAPDH-αFL-IGF1-αFT (see example 3), mp18/BamHI/GAPDH-αFLMut2-IGF1-αFT (see example 4) and mp18/BamHI/GAPDH-αFLG1G2G3G5-IGF1-αFT (see example 4). After ligation, an aliquot from each of the three ligation mixtures is transformed in *E. coli* HB101. Plasmid DNA of four individual transformants from each of the three ligations are analysed by SalI to determine the orientation of the BamHI fragments with respect to the SalI-BamHI pBR322 fragment. Plasmids yielding a 1147 bp fragment, with the pBR322 DNA at the 5' end of the promoter, are chosen and are named pDP34B/BamHI/GAPDH-αFL-IGF1-αFT, pDP34B/BamHI/GAPDH-αFLMut2-IGF1-αFT, and pDP34B/BamHI/GAPDH-αFLG1G2G3G5-IGF1-αFT.

EXAMPLE 6

Construction of Yeast Vectors Which Contain, on
the Same Plasmid, Expression Cassettes For
KEX2p and For IGF-1 with the Wild Type
α-Factor Leader Secretion Signal The yeast vector pDP34B (example 5) is digested to completion with BglII and treated with bacterial alkaline phosphatase. Plasmid pKS301 b (example 1) is digested with BamHI and the ~3210 bp fragment containing the complete KEX2 gene is isolated and ligated to the linearized vector pDP34B. An aliquot of the ligation mixture is transformed into *E. coli* HB101 and plasmid DNA of four transformants is examined by restriction analysis with BamHI and BglII. One clone with the expected restriction fragments is known as pDP34B/KEX2.

pDP34B/KEX2 is digested to completion with BamHI and treated with bacterial alkaline phosphatase.

A 1146 bp BamHI fragment containing the IGF-1 expression cassette isolated from pDP34A/GAPDH-αFL-IGF1-αFT (example 3) is ligated to linearized vector pDP34B/KEX2. After transformation, plasmid DNA of four clones is analysed with SalI and BamHI-BglII. One clone, with the promoter in the IGF-1 expression cassette 3' to the pBR322 SalI-BamHI fragment and the KEX2 gene in the opposite orientation to the IGF-1 cassette, is chosen and is named, pDP34B/KEX2/GAPDH-αFL-IGF1-αFT.

EXAMPLE 7

Construction of Yeast Vectors Which Contain, on
the Same Plasmid, Expression Cassettes For
KEX2p$_s$ and For IGF-1 with the Wild Type
α-Factor Leader Secretion Signal After digestion of plasmid pDPkexp (example 1) with SmaI, BamHI linkers [Boehringer Mannheim GmbH, Germany] are added, followed by digestion with BamHI and ScaI which allows isolation of a ~2560 bp BamHI fragment. This is ligated to linearized pDP34B. Analysis of plasmid DNA of transformants with BamHI and BamHI-BglII yields one clone with the expected restriction fragments which is named pDP34B/kexp.

The IGF-1 expression cassette is subcloned in the BamHI site of pDP34B/kexp in the same way as in example 6. Restriction analysis with SalI and BamHI-BglII yields different clones with the promoter of the IGF-1 expression cassette 3' to the pBR322 SalI-BamHI fragment and the soluble KEX2 in the opposite orientation to the IGF-1 cassette. One such clone is chosen and is named pDP34B/kexp/GAPDH-αFL-IGF1-αFT.

EXAMPLE 8

Construction of Yeast Vectors Which Contain, on
the Same Plasmid, Expression Cassettes For
KEX2p$_s$HDEL and For IGF-1 with the Wild Type
α-Factor Leader Secretion Signal pDPkexpHDEL (see example 2) is digested with BamHI, and after isolation of the about 2580 bp long fragment it is ligated to linearized pDP34B. Plasmid DNA of *E. coli* HB101 transformants are analysed with BamHI-BglII. One clone with the expected restriction fragments is named pDP34B/kexpHDEL.

The IGF-1 expression cassette is subcloned in the BamHI site of pDP34B/kexpHDEL in the same way as in example 6. Plasmid DNA of ampicillin resistant *E. coli* HB101 transformants is analysed with SalI and BamHI-BglII. One clone with the promoter of the IGF-1 expression cassette 3' to the pBR322 SalI-BamHI fragment and the soluble KEX2HDEL in the opposite orientation to the IGF-1 cassette is referred to as pDP34B/kex2pHDEL/GAPDH-αFL-IGF1-αFT.

EXAMPLE 9

Construction of Plasmids
pDP34B/KEX2/GAPDH-αFLMut2-IGF1-αFT,
pDP34B/kexp/GAPDH-αFLMut2-IGF1-αFT,
pDP34B/kexpHDEL/GAPDH-αFLMut2-IGF1-αFT,
pDP34B/KEX2/GAPDH-αFLG1G2G3G5-IGF1-αFT,
pDP34B/kexp/GAPDH-αFLG1G2G3G5-IGF1-αFT,
and
pDP34B/kexpHDEL/GAPDH-αFLG1G2G3G5-IGF1-αFT These plasmids are constructed in a way similar to the procedures detailed in examples 6, 7 and 8. The expression cassettes, BamHI fragments of GAPDH-αFLMut2-IGF1-αFT and GAPDH-αFLG1G2G3G5, are isolated from pDP34B/BamHI/GAPDH-αFLMut2-IGF1-αFT (see example 5) and pDP34B/BamHI/GAPDH-αFLG1G2G3G5-

IGF1-αFT (see example 5) and subcloned in yeast vectors already containing KEX2, or soluble KEX2 or soluble KEX2HDEL genes.

EXAMPLE 10

Construction of a kex2[31] Mutant of the Yeast Strain AB110 pKS301b (example 1) is cut at the unique BglII site in the KEX2 gene. A ~2920 bp BglII fragment from the plasmid YEp13 [J. Broach et al., Gene 8, 121–133 (1979)] is ligated to the linearized vector pKS301b. An aliquot of the ligation mixture is transformed in E. coli HB101. Plasmid DNA from twelve ampicillin resistant transformants are analysed with HindIII-EcoRI. One clone with the expected fragments is referred to as pUC19/kex2::LEU2. This plasmid has the coding sequence of the KEX2 gene disrupted by the functional LEU2 gene. pUC19/kex2::LEU2 is digested with BamHI to release the linear kex2::LEU2 fragment. The yeast strain AB110 is used for transformation (example 11) with the linearized DNA. Transformants are selected for leucine prototrophy. Genomic DNA of four LEU2+ transformants are digested by EcoRI-HindIII. To confirm that the genomic copy of KEX2 is indeed disrupted by the LEU2 gene, Southern blot analysis is performed. One yeast transformant with the expected restriction fragments is named AB110 kex2−.

EXAMPLE 11

Transformation of S. cerevisiae Strains AB110 and AB110 kex2−

Yeast transformation is carried out as described by Klebe et al. [Gene 25, 333–341 (1983)].

S. cerevisiae AB110 is transformed (see example 12) with the plasmids compiled hereinafter and the transformants are named as indicated:

| Plasmid | Transformant Name |
| --- | --- |
| pDP34B/GAPDH-αFL-IGF1-αFT (example 5) | yIG 1 |
| pDP34B/KEX2/GAPDH-αFL-IGF1-αFT (example 6) | yIG 2 |
| pDP34B/KEX2HDEL/GAPDH-αFL-IGF1-αFT (example 8) | yIG 3 |
| pDP34B/GAPDH-αFLMut2-IGF1-αFT (example 5) | yIG 4 |
| pDP34B/GAPDH-αFLG1G2G3G5-IGF1-αFT (example 5) | yIG 5 |

Three colonies of each of the transformants are selected and designated with an additional number (viz. yIG 1-1, yIG 1-2, yIG 1-3).

S. cerevisiae AB110 kex2− (see example 10) is transformed with the plasmids compiled hereinafter and the transformants are named as indicated:

| Plasmid | Transformant Name |
| --- | --- |
| pDP34B/GAPDH-αFL-IGF-αFT (example 5) | yIG 6 |
| pDP34B/KEX2/GAPDH-αFL-IGF1-αFT (example 6) | yIG 7 |
| pDP34B/KEX2/GAPDH-αFLMut2-IGF1-αFT (example 9) | yIG 8 |
| pDP34B/kexp/GAPDH-αFLMut2-IGF1-αFT (example 9) | yIG 9 |
| pDP34B/kexpHDEL/GAPDH-αFLMut2-IGF1-αFT (ex. 9) | yIG 10 |
| pDP34B/KEX2/GAPDH-αFLG1G2G3G5-IGF1-αFT (ex. 9) | yIG 11 |
| pDP34B/kexp/GAPDH-αFLG1G2G3G5-IGF1-αFT (ex. 9) | yIG 12 |
| pDP34B/kexpHDEL/GAPDH-αFLG1G2G3G5-IGF1-αFT (ex. 9) | yIG 13 |

Three colonies of each of the transformants are selected and designated with an additional number (viz. yIG 6-1, yIG 6-2, yIG 6-3).

EXAMPLE 12

Growth of Yeast Transformants in Shake-Flask Cultures and Quantitative/Qualitative Determination of IGF-1 Protein by High Performance Liquid Chromatography (HPLC) and Western Blots S. cerevisiae AB110 (Matα, his 4-580, leu2, ura 3-52, pcp 4-3, [cir°]) is described elswhere [P. J. Barr et al., J. Biol. Chem. 263, 16471–16478 (1988)]. A rich medium containing 6.5 g/l yeast extract, 4.5 g/l casamino acids and 30 g/l glucose is used as non-selective pre-culture medium. IGF-1 is expressed in the main culture which is a uracil-selective medium containing 1.7 g/l yeast nitrogen base supplemented with 30 g/l glucose, 8.5 g/l casamino acids and the required amino acids. Yeast transformants (see example 11) are grown at 30° C. on a rotary shaker at 180 rev./min. for 24 h in a 20 ml volume of the pre-culture medium and for 72 h in a 80 ml volume of main culture. Aliquot of cells are harvested and the secreted, active monomeric IGF-1 molecule in the culture medium is measured by HPLC and ELISA [K. Steube et al., Eur. J. Biochem. 198, 651–657 (1991)].

Aliquots of grown cultures are centrifuged for 2 minutes at 13000 x g. Cells are resuspended in 3×Laemmli buffer [6% SDS, 0.15M Tris pH6.8, 6 mM EDTA, 30% glycerol, 0.05% bromophenol blue] and lysed by vigorous shaking with glass beads followed by incubation of the samples for 3 minutes in a boiling water bath. Protein from the cell lysate are separated by SDS-PAGE using a 15% polyacrylamide gel [U.K. Laemmli, Nature 227, 680–685 (1970)]. Proteins are electroblotted onto nitrocellulose filters with the aid of a semi-dry blotter [Sartorius GmbH, Germany]. The transferred proteins are detected with anti-IGF-1 antibodies following the procedure supplied by the Bio-Rad immune assay kit [Bio-Rad, Richmond, Calif., USA].

EXAMPLE 13

A Comparison of Secreted and Intracellular IGF-1 Protein(s) by HPLC and Western Blot From Transformants yIG 1, yIG 6, and yIG 7

Secreted IGF-1 from transformants of plasmid pDP34B/GAPDH-αFL-IGF1-αFT (see example 5) in yeast strains AB110 (transformants yIG 1-1, yIG 1-2 and yIG 1-3) and AB110 kex2[31] (transformants yIG 6-1, yIG 6-2 and yIG 6-3) are compared by HPLC and the results are depicted in Table 1.

TABLE 1

| Transformant | HPLC titre in mg/l |
| --- | --- |
| yIG 1-1 | 8 |

TABLE 1-continued

| Transformant | HPLC titre in mg/l |
|---|---|
| yIG 1-2 | 7 |
| yIG 1-3 | 7 |
| yIG 6-1 | 0 |
| yIG 6-2 | 0 |
| yIG 6-3 | 0 |

Western blot analysis of intracellular protein from transformants yIG 6-1, yIG 6-2, and yIG 6-3 shows IGF-1 where the processing of the αFL has not occurred The results imply that no mature IGF-1 is secreted into the media from yeast strains which lack a functional copy of KEX2. When a functional copy of KEX2 is reintroduced on a plasmid, eg. pDP34/KEX2/GAPDH-αFL-IGF1-αFT (see example 6) into the yeast strain AB110 kex2⁻ (transformants yIG 7-1, yIG 7-2, and yIG 7-3) secreted IGF-1 is again observed.

EXAMPLE 14

A Comparison of Secreted IGF-1 Protein by HPLC and ELISA From Transformants yIG 1, yIG 2, and yIG 3

HPLC measures the amount of active, monomeric IGF-1 in the supernatant. ELISA determines the total amount of IGF-1-like species in the supernatant. Besides the monomer, ELISA quantifies the amounts of intermolecular disulfide bridged dimers and multimers, malfolded IGF-1, oxidized IGF-1, and other molecules. Table 3 shows a comparison of the HPLC titres and ELISA values of secreted IGF-1 from transformants co-expressing IGF-1 and KEX2 p (yIG 1 and yIG 2) and transformants co-expressing IGF-1 and soluble KEX2HDELp (yIG 3). The results are depicted in Table 2.

TABLE 2

| Transformants | HPLC titres in mg/l | ELISA values in mg/l |
|---|---|---|
| yIG 1 | 9 | 98 |
| yIG 2 | 8 | 92 |
| yIG 3 | 9 | 27 |

These results are the average values obtained from 3 individual strains from each of the 3 transformations. Co-expression of soluble KEX2HDEL shows that formation of molecules other than monomers have been drastically reduced.

EXAMPLE 15

A Comparison of Secreted IGF-1 Protein from Transformants yIG 1, yIG 4, yIG 8, yIG 9 and yIG 10 by HPLC Analysis The mutated leader sequence αFLMut2 does not allow secretion of IGF-1 in strain AB110. Glycosylated, unprocessed αFL-IGF-1 molecules accumulate inside the cell. From the nature of the glycosylation (only core-glycosylation observed), it is evident that these molecules have not traversed beyond the endoplasmatic reticulum due to mutations in the αFL sequence. Co-expression of IGF-1 using the αFLMut2 secretion signal, along with the three different forms of the KEX2 enzyme, KEX2, soluble KEX2 and soluble KEX2HDEL, in AB110 kex2⁻, shows that the soluble KEX2HDEL protein is different from the other two.

Western blot analysis of intracellular IGF-1-like proteins from transformants yIG 1, yIG 4, yIG 8, yIG 9 and yIG 10 reveals that only soluble KEX2HDEL protein releases mature IGF-1 from the intracellular pool.

EXAMPLE 16

Analysis of Secreted IGF-1 Protein from Transformants yIG 1, yIG 5, yIG 11, yIG 12 and yIG 13 by HPLC Analysis The mutated leader sequence αFLG 1G2G3G5 allows poor secretion of IGF-1 in strain AB110. Unglycosylated, unprocessed αFL-IGF-1 molecules accumulate inside the cell. It appears that these molecules lack the signal sequence of the αFL, which signifies that translocation into the ER has occurred. However, entry into the ER has not caused glycosylation of the three possible sequons (Asn-X-Ser/Thr) in the proregion of the αFL. Co-expression of IGF-1 with three different forms of the KEX2 enzyme (KEX2, soluble KEX2 and soluble KEX2HDEL) in AB110 kex2⁻ shows that the soluble KEX2HDEL protein expressed in yIG 13 is unique in permitting more mature IGF-1 to be released from the intracellular pool.

EXAMPLE 17

A Time Course Experiment to Study the Kinetics of Secretion of Monomeric IGF-1 from Yeast Transformants yIG 1, yIG 5 and yIG 13

The release of the proregion of the αFL from IGF-1 in the ER instead of in the Golgi may affect the total amount of monomeric IGF-1 secreted at different time points. It is probable that the proregion has a role in facilitating export of the unprocessed IGF-1 protein from the ER to the Golgi. To address this possibility, three individual strains from yIG 1, yIG 5 and yIG 13 are grown in shake flasks and the secretion of monomeric IGF-1 is measured by HPLC taking aliquots of supernatants from the yeast cultures after 40 h, 48 h, 60 h and 72 h. The average values obtained from three individual strains (e.g. yIG 1-1, yIG 1-2, yIG 1-3, and yIG 5-1, yIG 5-2, yIG 5-3, and yIG 13-1, yIG 13-2, yIG 13-3), belonging to each of the three transformations, yIG 1, yIG 5 and yIG 13, are shown in Table 3.

TABLE 3

| Strain | Secreted IGF-1 (mg/l) after | | | |
|---|---|---|---|---|
| | 40 h | 48 h | 60 h | 72 h |
| yIG 1 | 2.5 | 4 | 7 | 8.5 |
| yIG 5 | 0.8 | 1 | 1.2 | 1.5 |
| yIG 13 | 2.5 | 4.5 | 9.2 | 6 |

EXAMPLE 18

Analysis of Secreted IGF-1 by Western Blots Shows Appreciable Decrease of Dimeric Forms Using Soluble KEX2HDEL Protein Supernatants from yIG 1 and yIG 13 (example 17) have been analysed by Western blots under non-reducing and reducing conditions.

At time points 40 h, 48 h, and 60 h the formation of intermolecular disulphide bridged IGF-1 molecules is not observed using soluble KEX2HDEL protein. Only at 72 h does one see a negligible amount (barely visible on the blot) of dimeric IGF-1. However, strains expressing KEX2p do show dimers at every time point. These dimers can be reduced by dithiothreitol (DTT) implying that the dimers are indeed disulfide bonded.

5,501,975

DEPOSITED MICROORGANISMS

The following microorganism strains are deposited according to the Budapest Treaty at the Deutsche Sammlung von Mikroorganismen (DSM), Mascheroder Weg 1b, D-3300 Braunschweig (deposition dates and accession numbers given):

*Escherichia coli* JM109/pDP34: Mar. 14, 1988, DSM 4473.

*Escherichia coli* JM101/pKS301b: Jun. 25, 1990, DSM 6028.

---

What is claimed is:

1. A recombinant DNA molecule encoding an expression cassette for an ER-located "dibasic processing endoprotease" wherein the "dibasic processing endoprotease" consists of a "dibasic processing endoprotease" selected from the group consisting of YAP3 and KEX2p and an ER-retention signal selected from the group consisting of HDEL, KDEL and RDEL.

2. A recombinant DNA molecule according to claim 1 encoding an ER-located "dibasic processing endoprotease" consisting of a soluble "dibasic processing endoprotease" and an ER-retention signal.

3. A recombinant DNA molecule according to claim 1 encoding a protein selected from the group consisting of KEX2pHDEL, KEX2p$_s$HDEL and YAP3HDEL.

4. A hybrid vector comprising a recombinant DNA molecule according to claim 1.

5. A host cell transformed with a hybrid vector according to claim 4.

6. A host cell according to claim 5 which is stably transformed.

7. A process for the preparation of a recombinant DNA molecule according to claim 1, comprising deleting the DNA region coding for the membrane binding site from a plasmid containing the DNA coding for the dibasic endoprotease according to claim 1, and inserting, in proper reading frame, a DNA sequence coding for said retention signal in a proper reading frame.

8. A process for the preparation of a host cell comprising transforming a suitable host cell with a hybrid vector comprising an expression cassette encoding an ER-located "dibasic processing endoprotease" according to claim 7.

* * * * *